(12) United States Patent
Subramani et al.

(10) Patent No.: US 11,649,200 B2
(45) Date of Patent: May 16, 2023

(54) PROCESS AND APPARATUS FOR PRODUCTION AND SEPARATION OF ALCOHOLS AND OLIGOMERIZATION OF HYDROCARBON FEEDSTOCK

(71) Applicant: Indian Oil Corporation Limited, Mumbai (IN)

(72) Inventors: Saravanan Subramani, Faridabad (IN); Pushkar Varshney, Faridabad (IN); Reshmi Manna, Faridabad (IN); Madhusudan Sau, Faridabad (IN); Gurpreet Singh Kapur, Faridabad (IN); Sankara Sri Venkata Ramakumar, Faridabad (IN)

(73) Assignee: INDIAN OIL CORPORATION LIMITED, Mumbai (IN)

( * ) Notice: Subject to any disclaimer, the term of this patent is extended or adjusted under 35 U.S.C. 154(b) by 0 days.

(21) Appl. No.: 17/447,028

(22) Filed: Sep. 7, 2021

(65) Prior Publication Data
US 2022/0073441 A1 Mar. 10, 2022

(30) Foreign Application Priority Data
Sep. 5, 2020 (IN) .............................. 202021038395

(51) Int. Cl.
*C07C 29/04* (2006.01)
*C07C 7/04* (2006.01)
(Continued)

(52) U.S. Cl.
CPC ................ *C07C 29/04* (2013.01); *C07C 2/28* (2013.01); *C07C 7/00* (2013.01); *C07C 7/04* (2013.01);
(Continued)

(58) Field of Classification Search
CPC .. C07C 29/04; C07C 2/28; C07C 7/04; C07C 7/12; C07C 29/80; C07C 2531/08; Y02P 20/10
See application file for complete search history.

(56) References Cited

U.S. PATENT DOCUMENTS 3,351,635 A 11/1967 Kollar
4,100,220 A 7/1978 Bowman et al.
(Continued)

FOREIGN PATENT DOCUMENTS

CN 107663147 B 7/2019
WO 2003/033442 A1 4/2003

*Primary Examiner* — Rosalynd A Keys
(74) *Attorney, Agent, or Firm* — Workman Nydegger

(57) ABSTRACT

The present invention discloses an integrated process and an apparatus for production of various alcohols and Oligomerization of Olefinic feed stocks comprising butylenes and mixture thereof. In this process the combined light olefinic hydrocarbon feedstock is divided into two streams and contacted in two different reaction zones, viz. hydration and oligomerization. The mixture of alcohols and oligomer product from hydration reaction is separated and the bottom stream from separator is routed to oligomerization reaction zone in a controlled quantity as selectivity enhancer. Both the reaction zones are operated at different conditions. The product from oligomerization zone is further separated in to lighter and heavier components. Each reaction zone may comprise series of reactors filled with acidic catalysts comprising ion exchange resins.

20 Claims, 3 Drawing Sheets

(51) Int. Cl.
 *C07C 29/80* (2006.01)
 *C07C 7/12* (2006.01)
 *C07C 2/28* (2006.01)
 *C07C 7/00* (2006.01)

(52) U.S. Cl.
 CPC .............. *C07C 7/12* (2013.01); *C07C 29/80* (2013.01); *C07C 2531/08* (2013.01)

(56) References Cited

U.S. PATENT DOCUMENTS

| | | |
|---|---|---|
| 6,863,778 B2 | 3/2005 | Wang et al. |
| 7,038,101 B2 | 5/2006 | Nurminen et al. |
| 7,473,812 B2 * | 1/2009 | Peters .................... C07C 41/42 585/329 |
| 8,067,655 B2 | 11/2011 | Nichols et al. |
| 9,796,941 B2 * | 10/2017 | Xu ........................ C10L 1/1824 |
| 10,131,589 B2 | 11/2018 | Subramani et al. |
| 2003/0204122 A1 | 10/2003 | Loescher |
| 2006/0111598 A1 * | 5/2006 | Lin .......................... C07C 7/13 585/518 |
| 2007/0083069 A1 | 4/2007 | Candela et al. |
| 2007/0149839 A1 | 6/2007 | Rix et al. |

* cited by examiner

PROCESS AND APPARATUS FOR PRODUCTION AND SEPARATION OF ALCOHOLS AND OLIGOMERIZATION OF HYDROCARBON FEEDSTOCK

FIELD OF THE INVENTION

The present invention relates to an integrated process and apparatus for production of various alcohols and Oligomerization of Olefinic feed stocks comprising butylenes and mixture thereof. In this process the combined light olefinic hydrocarbon feedstock is divided into two streams and contacted in two different reaction zones, viz. hydration and oligomerization.

BACKGROUND OF THE INVENTION

Oligomerization of light olefins is a well-known process which utilizes different catalytic system for production of various desired end products. Oligomerization of isobutene, particularly dimerization of isobutene gained much importance in the past decade owing to the ban of methyl tertiary butyl ether (MTBE) in California and other states of US and Canada. Dimerization of isobutene to iso-octene is a well-known side reaction in the MTBE production process. This reaction is highly exothermic. In order to suppress dimerization reaction, methanol is always kept in excess over the stoichiometric ratio required for MTBE production. By reducing the methanol to isobutene mole ratio one can produce both the dimer product and MTBE in the same reactor. Iso-octene upon hydrogenation produces iso-octane, an ideal gasoline blending component. Conventionally various polar components are added during the dimerization process to control the selectivity of the reaction. Some of the polar components which are added during the dimerization reaction are tert-butyl alcohol (TBA), MTBE, Methanol, Ethanol, Isopropyl alcohol etc. TBA, most commonly used selectivity enhancer in isobutene dimerization process, is one of the costliest chemicals, which is produced commercially through well-known Oxirane process described in U.S. Pat. No. 3,351,635. Some of the patents like U.S. Pat. No. 8,067,655, WO2003/033442 made the efforts to recover the alcohol especially TBA using the energy and cost intensive process like extraction, dual distillation etc. as the TBA cannot be recovered easily owing to its azeotrope formation with water and also considering the cost of TBA.

U.S. Pat. No. 6,863,778B2 discloses a process for separation of tertiary butyl alcohol from diisobutylene using pressure swing azeotrophic distillation. In one of the columns which operates under higher pressure, a side cut is drawn in which the azeotrope of Diisobutylene and TBA is drawn and sent to second distillation column where the Diisobutylene and TBA is separated. US application 20030204122 A1 discloses a process for recovery of TBA from Diisobutylene by extracting the TBA from isobutene with water in a column and subsequently contacting the mixture with other hydrocarbon stream containing isobutene. The stream containing isobutene and TBA is recycled back to the reactor, whereas water is removed from bottom of the column. CN107663147B discloses a process for separating tert-butanol and diisobutylene mixture by selective adsorption of TBA using adsorbent and the adsorbent used is continuously regenerated in cyclic basis.

U.S. Pat. No. 7,038,101B2 discloses a method for recovery of a mixture of $C_3$-$C_6$ alcohol from the iso-octene dimerization product using liquid extraction with water, and subsequent extraction of the mixed C3-C6, alcohol from the water stream using the net $C_4$ hydrocarbon stream to the isobutylene dimerization reaction section. In this process, the recycle of $C_3$-$C_6$ alcohol to the dimerization section is achieved in two liquid extraction steps.

US 20070083069A1 discloses a process for the oligomerization of an olefin in the presence of a selectivity enhancing alcohol modifier wherein the modifier is formed by the reaction of olefin and water in a first reaction, and the thus formed modifier substantially free of water is separated and passed to a second reaction wherein olefin is oligomerized in the presence of the said modifier. In situ production of TBA in a dimerization reactor as described in U.S. Pat. No. 4,100,220, will make the progress of both the reaction competitive and result in undesired product selectivity w.r.t TBA and dimer. The prior art describes that the water to isobutene mole ratio should be maintained less than 0.06 and the addition of water greater than this value will tend to shift the reaction from dimerization to hydration. This is the major drawback of the prior art due to which the selectivity of dimer product cannot be increased beyond 73% (Ref Table-II), whereas selectivity of undesired trimer product ($C_{12}$ olefins) is increased wherever the water to isobutene mole ratio is maintained less than 0.06. Also, precise dosing of water in such a low quantity to maintain the ratio within the limit is not only very difficult to practice in the commercial scale but will also create the non-uniform contact between the catalyst and reactants i.e. some part of the catalyst in the reactor will be wet with the water where the hydration reaction predominates whereas the other part of the catalyst remaining dry will promote oligomerization reaction leading to non-uniform temperature profile along the reactor. The different reaction environment required for oligomerization and hydration reaction cannot be maintained in a single reactor as described in the prior art.

U.S. Ser. No. 10/131,589B2 discloses a process for simultaneous production of alcohol and oligomer product, in particular for production of oligomer product in presence of tert-butyl alcohol (TBA) and isopropyl alcohol (IPA) to achieve the desired selectivity of dimer product. Also, it discloses the process for production of TBA, IPA and other alcohols in hydration reaction zone and oligomer product in oligomerization reaction zone. Further it produces IPA, which in combination with TBA maximizes the selectivity of dimer product in oligomerization reaction zone. In order to produce IPA and TBA maximum wetting is required in the hydration reaction zone and also a separate stream comprising propylene is required which will make the process complicated Catalyst deactivation and/or poisoning during oligomer production is generally reported. The excess tert-butyl alcohol (TBA), water and/or other impurities are generally responsible for catalyst deactivation and/or poisoning. Further, the catalyst deactivation and/or poisoning hamper the smooth production of oligomers from an olefinic feedstock. Moreover, less TBA than the requirements in the oligomerization zone leads to formation of heavier oligomers which in turn deposited over the catalyst and blocks the catalyst pores resulting deactivation of the catalyst. Accordingly, there is a need of a process for simultaneous production of alcohols, oligomers from an olefinic C4 feedstock, wherein, a precise quantity of the tert-butyl alcohol (TBA) is transferred to the oligomerization reaction zone without any excess TBA, water and any other hydrocarbon. Further, there is a need of a process and apparatus which remove impurities from olefinic feedstock, improve catalyst life, and performance of catalyst in hydration and oligomerization zone by using of premixing zone or pressure reduction.

SUMMARY OF THE INVENTION

In oligomerization reaction using ion exchange resin as catalyst, particularly dimerization of isobutene to iso-octene, Tertiary butyl alcohol (TBA) is used as selectivity enhancer for dimer product. However, handling TBA is a problem even at normal atmospheric conditions due to its low melting point (25° C.). In order to overcome this, TBA is conventionally produced in situ in the dimerization reactor by injecting small quantity of water, which reacts with isobutene present in the feed to produce TBA. This procedure of in situ production of TBA in the same reactor usually creates lot of operational problems such as, difficulty in maintaining precise low quantity dosing of water, non-uniform temperature distribution and also nonselective reaction as production of TBA through hydration and oligomerization of olefins require different reaction environment. Even if there is a separate hydration reaction zone for production of TBA to overcome the above-mentioned issue, it will be difficult to control the carryover of water during process upsets or during the initial startup, which acts as a temporary poison and suppress the oligomerization reaction, in the oligomerization reaction zone. Also, when the TBA and $C_4$ from hydration reaction zone is routed to oligomerization zone it is not possible to analyze the hydration reactor product, as it is a mixture of gas and liquid due to which estimation of exact quantity of TBA sent to the oligomerization reactor is not feasible, which in turn affects the precise control of TBA in oligomerization reaction zone, thereby product yield and quality.

Accordingly, the present invention provides a process for simultaneous production of alcohols, oligomers from an olefinic C4 feedstock. Wherein, the said olefinic C4 feedstock is divided into two streams and contacted with acidic catalysts including ion exchange resin catalysts in two different reaction zones, which are operating at different conditions specifically to favour the production of TBA and other alcohols and small portion of oligomer product in first reaction zone and the oligomerization reaction in the second reaction zone. Before dividing into two streams, the entire feedstock is routed to DeMet reaction zone where the impurities present in the feedstock such as nitrogenous compounds, metals have been removed.

The product after the hydration reaction zone is routed to a separator where the heavier products which comprises majorly alcohols and a small portion of oligomer product is separated from the lighter products comprising the unconverted C4.

Precise quantity of recovered alcohol from the separator is routed to oligomerization reaction zone after mixing with $C_4$ feedstock comprising olefins at the inlet of oligomerization reaction zone depending upon the operating conditions. As TBA, which is sent to the oligomerization zone in precise quantity containing only minimal quantity of other hydrocarbons, is consumed in the reaction zone, no excess TBA/water is carried over in the main product as mentioned in the prior arts, which again requires energy intensive and cost intensive separation process. The remaining excess quantity of product from separator is routed to storage tanks for future usage. Excess TBA/water also suppresses the oligomerizatin reaction and reduces the yield of product.

The TBA and other alcohols are produced in hydration reaction zone in such a way that it will form azeotrope with the other hydrocarbon and the freezing point of the mixture decreases below 25° C. Accordingly, the storage issue of TBA is also resolved by the process of present invention. Also, it is surprisingly seen that during separation, water is collected at the top of column along with the lighter components which is further removed by simple decantation by allowing requisite settling time.

The avoidance of carryover of water into the oligomerization reaction zone protects the catalyst from deactivation and also ensures smooth operation.

This makes the entire process an economically viable one and also completely eliminates the above-mentioned disadvantages of the prior arts.

Technical Advantages of the Invention

The present invention has the following advantage over the prior arts:

One advantage of the present invention is to operate the hydration and oligomerization reaction zone with high degree of flexibility for controlling the desired product as both the reaction zone operates with independent reactor and separators.

Another advantage of the present invention is to control the selectivity in the oligomerization reactor by varying the concentration of alcohol from the hydration reactor, which cannot be controlled when the water is added in the same oligomerization reactor for in situ production of alcohol or when there is no separator for hydration reaction zone.

Yet another advantage of present invention is to offer the flexibility for maintaining the reaction environment conducive for hydration and oligomerization application favoring the selective production of respective alcohols and oligomer product.

Another advantage of present invention is avoiding the carryover of water into the oligomer reaction zone which in turn avoids the temporary deactivation of catalyst in the oligomer reaction zone.

Yet another advantage of the present invention is the premixing zone like mixing valve, static mixer which makes the alcohol and hydrocarbon mixture in homogenous form and facilitates the uniform distribution of TBA/hydrocarbon mixture in the oligomerization reaction zone and avoids hot spot. This reduces the deactivation rate of oligomerization catalyst.

Another advantage of the present invention is the removal of impurities like metals, nitrogenous components etc by passing the feed through DeMet reaction zone prior to routing in hydration and oligomerization reaction zone, which increases the catalyst life and performance of both the catalyst in hydration and oligomerization zone.

Objectives of the Invention

It is the primary objective of the present invention which covers a process for simultaneous production of alcohols and oligomer using ion exchange resin catalyst in a multiple reactor and separation system.

It is further objective of the present invention is the flexibility to operate the two different reaction zones at different operating conditions favorable for hydration and oligomerization reactions, respectively.

It is further objective of the present invention is that the hydrocarbon feedstock to the hydration reactor reacts with water, along with isobutene the other butylenes present in the light hydrocarbon feedstock also get converted partly to respective alcohols which increases the selectivity of dimer product to greater than 90% in the oligomerization reactors.

It is further objective of the present invention is that to remove water from top of the hydration reactor separation column as the water surprisingly ends up in the boot of reflux drum of the column.

It is further objective of the present invention is that the excess flow of alcohol to oligomer reaction zone is avoided, by adding precise quantity of TBA and other alcohols to oligomer reaction zone which is only possible due to separation of $C_4$ and other lighter hydrocarbons from alcohol and other oligomer product.

It is further objective of the present invention to remove the impurities present in the $C_4$ feedstocks by passing the feed through DeMet reaction zone wherein the impurities like metals, nitrogenous components have been removed, which increases the catalyst life and performance of catalyst in hydration and oligomerization zone.

It is further objective of the present invention to provide a premixing zone like mixing valve, static mixer which makes the alcohol and hydrocarbon mixture in homogenous form and facilitates the uniform distribution of TBA/hydrocarbon mixture in the oligomerization reaction zone and avoids hot spot. This reduces the deactivation rate of oligomerization catalyst.

BRIEF DESCRIPTION OF THE DRAWING

To further clarify advantages and aspects of the invention, a more particular description of the invention will be rendered by reference to specific embodiments thereof, which is illustrated in the appended drawing(s). It is appreciated that the drawing(s) of the present invention depicts only typical embodiments of the invention and are therefore not to be considered limiting of its scope.

DETAILED DESCRIPTION OF THE INVENTION

Figure 1:
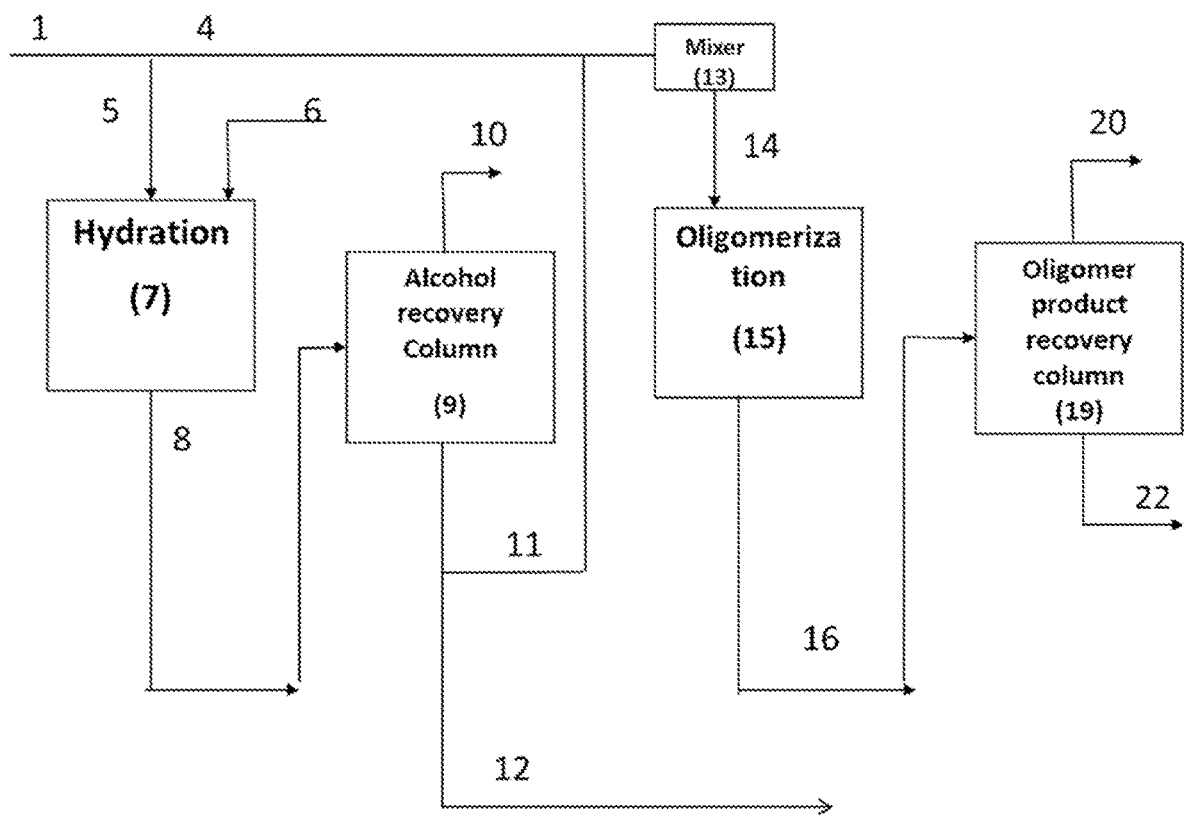
FIG. 1: illustrates a schematic process flow diagram of the invented process without a pressure reduction zone and de-metallization reaction zone.

According to the main embodiment, the present invention covers a process for simultaneous production of alcohols and oligomer using ion exchange resin catalyst in a multiple reactor and separation system.

Specifically, the present invention provides a process for simultaneous production of alcohols, oligomers from an olefinic C4 feedstock (1). The process includes an impurity removal step further including passing the olefinic C4 feedstock (1) through a de-metallization reaction zone (2), wherein, the de-metallization reaction zone (2) removes at least one impurity component from the said olefinic C4 feedstock (1). The at least one impurity component is selected from a metal impurity component such as iron, calcium, sodium ionic components, a nitrogenous component such as nitriles, amines etc., and a basic component such as sodium hydroxide, or a combination thereof. The impurity component in the de-metallization reaction zone (2) is removed by using low active ion exchange resin catalyst. The ion exchange resin catalyst is selected from a group containing the total exchange capacity of 3.5-4.0 milliequivalent per dry gram of catalyst, styrene-divinyl benzene copolymer in the backbone and sulfonic acid as active component. The impurities are absorbed in the catalyst bed by ion exchange with the catalyst ionic form and the impurity. Then dividing the olefinic C4 feedstock (3) as obtained from the de-metallization reaction zone (2) into a first stream (5), and a second stream (4).

Further, the process of the present invention includes a hydration step further including passing the said first stream (5) through a hydration reaction zone (7), wherein, an acidic catalyst and water (6) hydrate an olefinic C4 feedstock of the first stream (5) into heavier products including a mixture of a plurality of alcohol compounds, and a plurality of oligomer products. The plurality of alcohol compounds includes tert-butyl alcohol (TBA), and other lighter alcohols such as sec-butyl alcohol, 1-butanol, 2-butanol, isobutanol etc., wherein, the tert-butyl alcohol (TBA) form azeotropes with hydrocarbons of the olefinic C4 feedstock and having freezing point below 25° C.

Further, the process includes routing of a hydration product (8) into an alcohol recovery column (9), wherein, the alcohol recovery column (9) separates the said heavier products from an unconverted olefinic C4 feedstock (10). In the alcohol recovery column (9) an unreacted water along with lighter components is collected at top of the said alcohol recovery column (9), the said unreacted water is removed by a decantation process. Further, the unconverted olefinic C4 feedstock (10) is transferred to the oligomer product recovery column (19) downstream of a pressure reduction zone (17).

Further, the process of the present invention includes an oligomerization step including passing the said second stream (4) through an oligomerization reaction zone (15) having an ion exchange resin catalyst, wherein, the second stream (4) passes through a mixer (13) before going into the oligomerization reaction zone (15). The oligomerization reaction zone (15) in the presence of an ion exchange resin catalyst converts a mixer stream (14) into an oligomer compound. Further, a precise quantity of the tert-butyl alcohol (TBA) (11) is transferred to the oligomerization reaction zone (15) after mixing with an olefinic C4 feedstock of the second stream (4) in the said mixer (13), and an extra quantity of the tert-butyl alcohol (TBA) (12) is transferred to a storage unit. The precise quantity of the tert-butyl alcohol (TBA) (11) is completely consumed in the oligomerization reaction zone (15). The oligomerization reaction zone (15) without any unreacted water protects the ion exchange resin catalyst from deactivation.

The acidic catalyst used in the hydration reaction zone (7) and the oligomerization reaction zone (15) is selected from a group containing high active cation exchange resin having the total exchange capacity of >5.0 milliequivalent per dry gram of catalyst, styrene-divinyl benzene in the backbone and sulfonic acid group in the active sites such as Amberlyst 15, Amberlyst 35, INDION 180, Tulsion® T62MP etc.

Thereafter, an oligomerization product stream (16) is routed into an oligomer product recovery column (19), wherein, the oligomerization product stream (16) passes through a pressure reduction zone (17) before going into the oligomer product recovery column (19). The pressure reduction zone (17) reduces the pressure of the oligomerization product stream (16) to 5-7 bar. Further, the oligomer product recovery column (19) separates a pressure reduction zone stream (18) into an unreacted olefinic C4 component (20) and an oligomer product (22).

Further, the unreacted olefinic C4 component (20) is transferred to the oligomerization reaction zone (15), wherein, the said unreacted olefinic C4 component (20) acts as a coolant to remove the exotherm in the oligomerization reaction zone (15) to increase the overall yield of oligomer product.

The ratio of the said first stream (5) passing through a hydration reaction zone (7) and the second stream (4) passing through an oligomerization reaction zone (15) ranges from 0.01:1 to 0.3:1. In the detailed embodiment, the aforesaid process (ref: FIG. 1) wherein $C_4$ feed stock comprising isobutene (1) as one of the components is divided into two portions (4) & (5) and routed to the reaction zone (7) and (15) respectively, whereas the stream (4) enters the pre-mixing zone (13) before entering into reaction zone (15). The ratio of feed to (7) and (15) varies from 0.01:1 to 0.3:1. Water (6), preferably DM water, else any water free from metals and other contaminants e.g., steam condensate is added to the reaction zone (7) for hydration of the respective olefins to corresponding alcohols. Water is added in such a quantity to produce the alcohol and oligomer mixture that will not freeze in normal storage conditions. The product (8) from the reaction zone (7) is routed to separator (9) (distillation column or any conventional separation system), wherein, the unreacted $C_4$ (10) is removed from the top and routed to downstream section like LPG pool or any other units etc., further the bottom stream from the separator (9) which comprises alcohol and oligomer product is divided into two streams (11) and (12), stream (11) is routed to premixing zone (13) where the $C_4$ stream (4) is mixed with the stream (11) to make the homogenous mixture of alcohol, along with other hydrocarbons. Stream (12) is routed to storage or to any other units for further processing.

In the detailed embodiment, the aforesaid process wherein the stream (14) from premixing zone enters into the reaction zone (15) where the oligomerization reaction of $C_4$ olefins takes place. Stream (16) which comprises the oligomer product along with unreacted feed enters into the separator (19) (Distillation column or any conventional separation system) where in the unreacted $C_4$ components is separated from the oligomer product. The unreacted $C_4$ components (20) is routed to downstream section like LPG pool, Alkylation units etc. Stream (22) is routed to gasoline pool directly or to any other downstream units.

Figure 2:
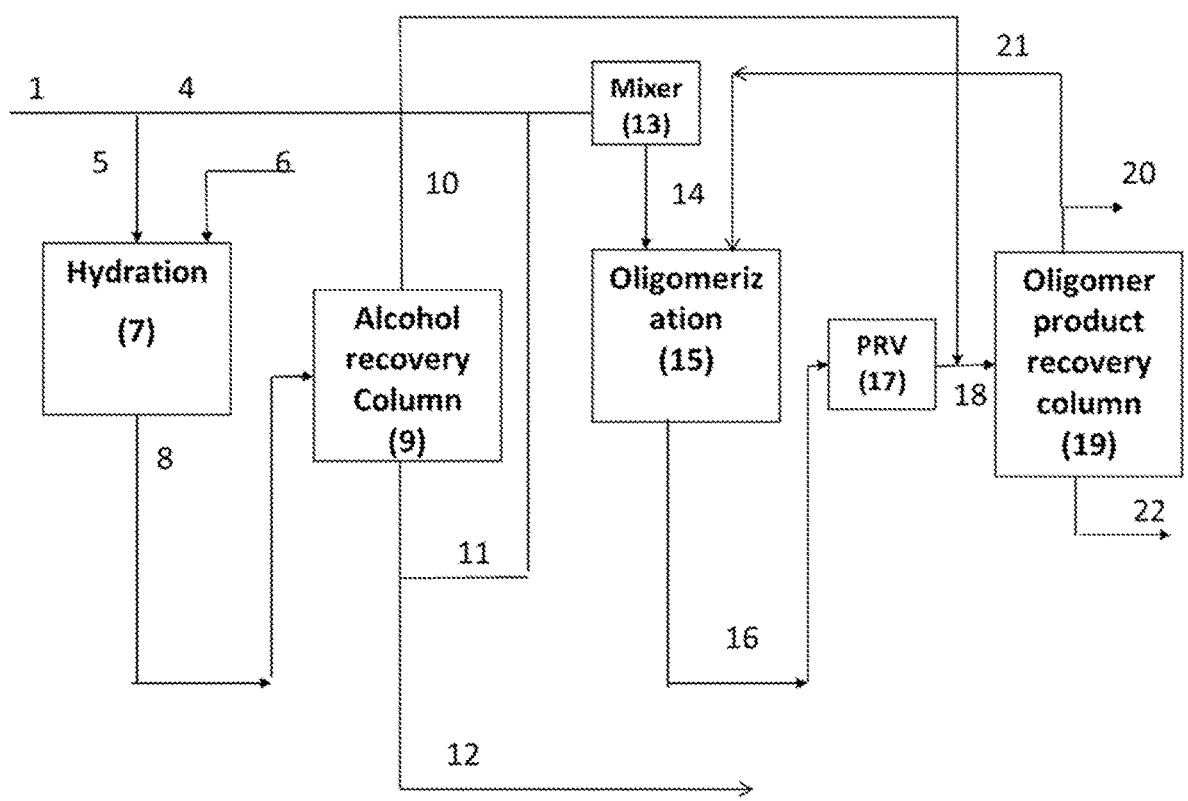
FIG. 2: illustrates a schematic process flow diagram of the invented process without a de-metallization reaction zone.

In the detailed embodiment, the aforesaid process (Ref: FIG. 2) wherein $C_4$ feed stock comprising isobutene (1) as one of the components is divided into two portions (4) & (5) and routed to the reaction zone (7) and (15) respectively, whereas the stream (4) enters the pre-mixing zone before entering into reaction zone (15). The ratio of feed to (7) and (15) varies from 0.01:1 to 0.3:1. Water (6), preferably DM water, else any water free from metals and other contaminants e.g. steam condensate is added to the reaction zone (7) for hydration of the respective olefins to corresponding alcohols. Water is added in such a quantity to produce the alcohol and oligomer mixture that will not freeze in normal storage conditions. The product (8) from the reaction zone (7) is routed to separator (9) (Distillation column or any conventional separation system) where the un-reacted $C_4$ (10) is removed from the top and routed to downstream of pressure reduction zone (17), further the bottom stream from the separator (9) which comprises alcohol and oligomer product is divided into two streams (11) and (12), stream (11) is routed to premixing zone (13) where the $C_4$ stream (4) is mixed with the stream (11) to make the homogenous mixture of alcohol, along with other hydrocarbons. Stream (12) is route to storage or to any other units for further processing.

In the detailed embodiment, the aforesaid process wherein stream (14) from premixing zone enters in the reaction zone (15) where the Oligomerization reaction of $C_4$ olefins takes place. Stream (16) which comprises the oligomer product along with un-reacted feed enters in the pressure reduction zone (17) where the pressure is reduced to 5-7 bar before routing to the separator (19) (Distillation column or any conventional separation system), wherein, the un-reacted $C_4$ components is separated from the oligomer product. The un-reacted $C_4$ stream (10) also enters the column post pressure reduction zone (17). The un-reacted $C_4$ components (20) is routed to downstream section like LPG pool, Alkylation units etc. Stream (22) is routed to gasoline pool directly or to any other downstream units. A portion of stream (20), which is stream (21) is recycled back to the oligomerization reactors directly which acts as a diluent/coolant to remove the exotherm in the reactor and also to increase the overall yield of oligomer product.

Figure 3:
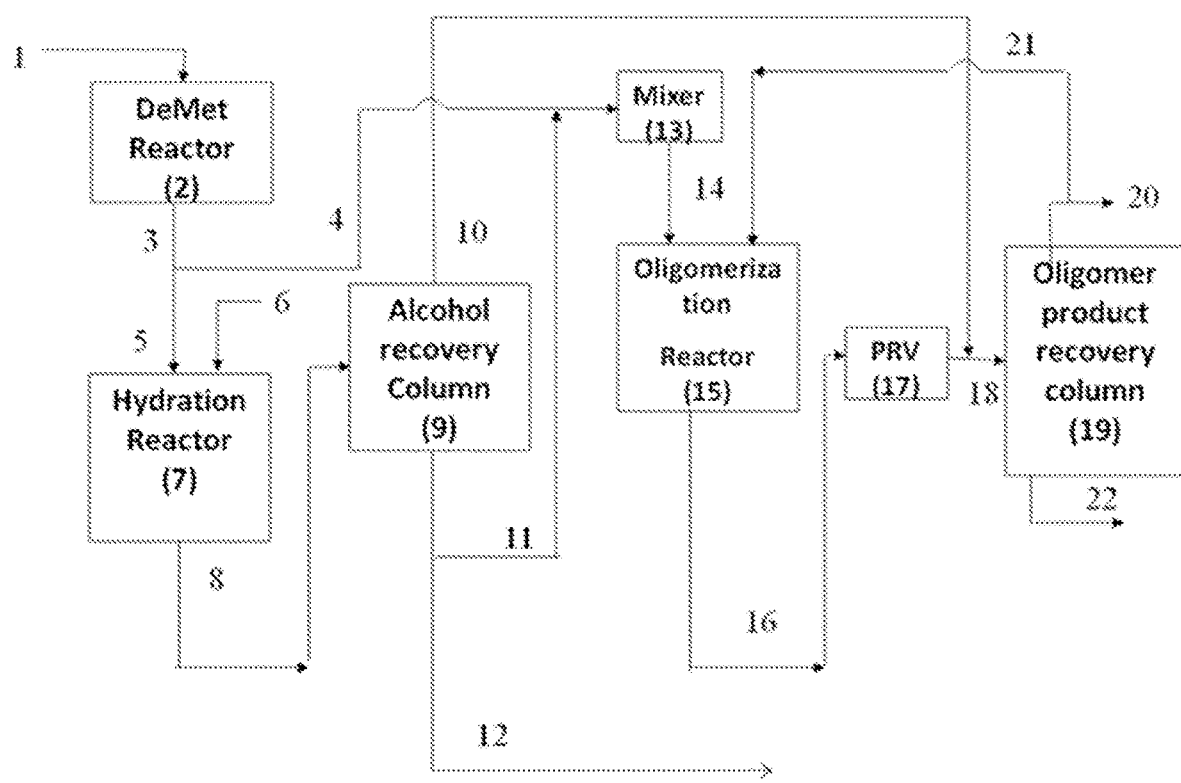
FIG. 3: illustrates a schematic process flow diagram of the invented process with pressure reduction zone and de-metallization reaction zone.

In the detailed embodiment, the aforesaid process (Ref: FIG. 3) wherein $C_4$ feed stock comprising isobutene (1) as one of the component is fed in to the DeMET reactor (2) reaction zone wherein the feed metal, nitrogenous components and other impurities like basic components were removed and the stream (3) which comes out of reaction zone (2) is divided into two portions (4) & (5) and routed to the reaction zone (7) and (15) respectively, whereas the stream (4) enters the pre-mixing zone before entering into reaction zone (15). The ratio of feed to (7) and (15) varies from 0.01:1 to 0.3:1. Water (6), preferably DM water, else any water free from metals and other contaminants e.g., steam condensate is added to the reaction zone (7) for hydration of the respective olefins to corresponding alcohols. Water is added in such a quantity to produce the alcohol and oligomer mixture that will not freeze in normal storage conditions. The product (8) from the reaction zone (7) is routed to separator (9) (Distillation column or any conventional separation system) where the un-reacted $C_4$ (10) is removed from the top and routed to downstream of pressure reduction zone (17), further the bottom stream from the separator (9) which comprises alcohol and oligomer product is divided into two streams (11) and (12), stream (11) is routed to premixing zone (13) where the $C_4$ stream (2) is mixed with the stream (11) to make the homogenous mixture of alcohol, along with other hydrocarbons. Stream (12) is routed to storage or to any other units for further processing.

In the detailed embodiment, the aforesaid process wherein stream (14) from premixing zone enters into the reaction zone (15) where the Oligomerization reaction of $C_4$ olefins takes place. Stream (16) which comprises the oligomer product along with un-reacted feed enters into the pressure reduction zone (17) where the pressure is reduced to 5-7 bar before routing to the separator (19) (Distillation column or any conventional separation system) where in the un-reacted $C_4$ components is separated from the oligomer product. The un-reacted $C_4$ stream (10) also enters the column post pressure reduction zone (17). The un-reacted C4 components (20) is routed to downstream section like LPG pool, Alkylation units etc. Stream (22) is routed to gasoline pool directly or to any other downstream units. A portion of stream (20), which is stream (21) is recycled back to the oligomerization reactors directly which acts as a diluent/coolant to remove the exotherm in the reactor and also to increase the overall yield of oligomer product.

Example—1

This example (data mentioned in table 1) shows the effect of water carryover in a distillation column when the hydrocarbon along with some minimal quantity of water is sent to the distillation column which is operated at 51° C. & 160° C. top and bottom temperature, respectively. Feed to the column is a mixture of oligomer product and unreacted $C_4$ from the reactor, wherein the column separates $C_4$ mixture from the top and Oligomer product from the bottom.

TABLE 1

| Water rate in feed, kg/h | Water Concentration in feed, ppm | Water in top, kg/h | Water in bottom, kg/h |
|---|---|---|---|
| 0 | 0.0 | 0 | 0 |
| 0.5 | 10.2 | 0 | 0.5 |
| 5 | 102.0 | 0 | 5 |
| 50 | 1019.7 | 0.01 | 49.99 |
| 500 | 10197.0 | 0.01 | 499.99 |

Further, the present invention provides an apparatus for simultaneous production of alcohols, and oligomers from an olefinic C4 feedstock (1). The said apparatus includes a de-metallization reaction zone (2) for removing at least one impurity component from the said olefinic C4 feedstock (1), wherein, the olefinic C4 feedstock (3) as obtained from the de-metallization reaction zone (2) is divided into a first stream (5), and a second stream (4) which passes through a mixer (13) to provide a mixer stream (14).

The apparatus includes a hydration reaction zone (7) to carry out a hydration reaction in the presence of an acidic catalyst and water (6), wherein, the hydration reaction converts the olefinic C4 feedstock of the first stream (5) into heavier products including a mixture of a plurality of alcohol compounds, and a plurality of oligomer products. The plurality of alcohol compounds includes a tert-butyl alcohol (TBA), and other lighter alcohols, wherein, the tert-butyl alcohol (TBA) form azeotropes with hydrocarbons of the olefinic C4 feedstock and having freezing point below 25° C.

The apparatus includes an alcohol recovery column (9) to separate the said heavier products from an unconverted olefinic C4 feedstock (10). The unconverted olefinic C4 feedstock (10) is transferred to the oligomer product recovery column (19) downstream of a pressure reduction zone (17). Further, in the alcohol recovery column (9) an unreacted water along with lighter components is collected at top of the said alcohol recovery column (9), the said unreacted water is removed by a decantation process.

An oligomerization reaction zone (15) to carry out an oligomerization reaction of the mixer stream (14) in the presence an ion exchange resin catalyst, wherein, the oligomerization reaction zone (15) output an oligomerization product stream (16). A precise quantity of the tert-butyl alcohol (TBA) (11) is transferred to the oligomerization reaction zone (15) after mixing with an olefinic C4 feedstock of the second stream (4) in the said mixer (13), and an extra quantity of the tert-butyl alcohol (TBA) (12) is transferred to a storage unit.

The apparatus includes an oligomer product recovery column (19) and a pressure reduction zone (17), wherein, the oligomerization product stream (16) passes through the pressure reduction zone (17) before going into the oligomer product recovery column (19). The pressure reduction zone (17) reduces the pressure of the oligomerization product stream (16) to 5-7 bar.

Yield Data

Example—2

The below table-2 shows the composition of the C4 feed and mention the components and their weight percent composition.

TABLE 2

| Components | Composition, Wt. % |
|---|---|
| i-Butane | 30.76 |
| n-Butane | 9.03 |
| Iso-Butene | 19.1 |
| Trans-2-Butene | 13.28 |
| Cis-2-Butene | 10.24 |
| 1-Butene | 11.97 |
| Propane | 3.49 |
| Propylene | 0.83 |
| I-pentane | 0.61 |
| C6+ | 0.65 |

Example—3

The below table-3 shows the effect of TBA concentration at the inlet of oligomerization reaction zone on the conversion of $C_4$ to higher boiling liquid products and selectivity towards dimers.

TABLE 3

| Run No. | TBA content in C4 feed, Wt. % | Temperature, ° C. | Pressure, Bar | Yield of oligomer product, Wt. % | Selectivity of dimers, Wt. % |
|---|---|---|---|---|---|
| 1 | 0.18 | 81.07 | 14.5 | 22.30 | 56.72 |
| 2 | 0.34 | 79.78 | 14.5 | 24.78 | 62.23 |
| 3 | 0.72 | 79.34 | 14.5 | 20.71 | 92.45 |
| 4 | 1.92 | 79.64 | 14.5 | 13.97 | 95.53 |
| 5 | 4.23 | 77.57 | 14.5 | 9.50 | 96.92 |

This above table-3 and example shows that with the increase in TBA concentration, the yield of oligomer product decreases, hence, precise quantity of TBA to be added at the oligomerization reactor inlet to maintain the yield of the oligomer product.

At normal temperature, water molecules are bridged into the network of sulfonic acid groups of the ion exchange resin catalyst used in the said process by hydrogen bonding, where it would experience strong polarizing forces which could lead to proton transfers. However, during the dimerization of isobutene at the elevated temperature, hydrolysis occurs by the water carried over through the C4 feed which results in the dissociation of the sulfonic acid groups from the resin structure. The sulfonic acid group leaches out from the catalyst resulting the deactivation of the catalyst.

Example—4

The below table-4 shows the effect of poisoning of Oligomerization catalyst.

TABLE 4

| Catalyst Descriptions | Density Kg/m3 | Total acid capacity meq/gm | C % | H % | N % | S % | Metal Contents | IR Spectra Comparison |
|---|---|---|---|---|---|---|---|---|
| Fresh Catalyst | 653 | 5.24 | 37.1 | 5.1 | <0.1 | 17 | <10 ppm | Styrene DVB sulfonic acid type matrix is observed in fresh as well as in spent catalysts |
| Spent Catalyst 1 | 550 | 3.01 | 55.3 | 7.1 | 3.8 | 12.2 | Ca = 59 ppm<br>Fe = 529 ppm<br>Mg = 27 ppm<br>Mo = 61 ppm<br>Na = 62 ppm | Presence of Hydrocarbon and amine type moieties observed. |
| Spent catalyst 2 | 553 | 2.24 | 64.3 | 6.8 | 1.6 | 11.1 | Ca = 261 ppm<br>Fe = 2348 ppm<br>Mg = 44 ppm<br>Mn = 29 ppm<br>Mo = 37 ppm<br>Na = 44 ppm | Presence of Hydrocarbon and amine type moieties observed. |

Commercial spent catalysts obtained from a refinery and its detailed characterization has been done and compared with the fresh catalyst. It is evident from the above analysis that the metals, nitrogenous compounds present in the feed stream slowly deposits on the catalyst and affects its activity. The heavier hydrocarbon formation which is evident from carbon analysis of spent catalysts is due to the formation of heavier oligomers (Due to low TBA at Oligomerization reactor inlet) inside the pores of the catalyst and affects the activity. Hence, in order to increase the life of hydration and oligomerization reactor catalyst De-Met reactor is used in the process of present invention with low active catalyst, which operates at 30-45° C. and at a pressure of 16-20 bar which absorbs all the metal and nitrogenous impurities. Formation of heavier oligomer is minimized by controlling the precise quantity of TBA at the oligomerization reactor inlet.

We claim:

1. A process for simultaneous production of alcohols and oligomers from an olefinic C4 feedstock, the process comprising steps of:
    passing the olefinic C4 feedstock through a de-metallization reaction zone, wherein the de-metallization reaction zone removes at least one impurity component from the olefinic C4 feedstock;
    dividing the olefinic C4 feedstock as obtained from the de-metallization reaction zone into a first stream, and a second stream;
    passing the first stream through a hydration reaction zone, wherein an acidic catalyst and water hydrate the first stream to form a hydration product, wherein the hydration product comprises heavier products comprising a mixture of a plurality of alcohol compounds, and a plurality of oligomer products;
    routing the hydration product into an alcohol recovery column, wherein the alcohol recovery column separates the heavier products from an unconverted olefinic C4 feedstock;
    passing the second stream and a precise quantity of recovered alcohol through an oligomerization reaction zone having an ion exchange resin catalyst, wherein the second stream and the precise quantity of recovered alcohol passes through a mixer before going into the oligomerization reaction zone; and
    routing of an oligomerization product stream into an oligomer product recovery column, wherein the oligomerization product stream passes through a pressure reduction zone before going into the oligomer product recovery column.

2. The process as claimed in claim 1, wherein the at least one impurity component is selected from a metal impurity component, a nitrogenous component, and a basic component, or a combination thereof.

3. The process as claimed in claim 1, wherein the plurality of alcohol compounds comprise a tert-butyl alcohol (TBA), and lighter alcohols, wherein, the tert-butyl alcohol (TBA) form azeotropes with hydrocarbons of the olefinic C4 feedstock and having freezing point below 25° C.

4. The process as claimed in claim 1, wherein the oligomerization reaction zone in presence of an ion exchange resin catalyst converts a mixer stream into an oligomer compound.

5. The process as claimed in claim 1, wherein a precise quantity of the tert-butyl alcohol (TBA) is transferred to the oligomerization reaction zone after mixing with an olefinic C4 feedstock of the second stream in the mixer, and an extra quantity of the tert-butyl alcohol (TBA) is transferred to a storage unit.

6. The process as claimed in claim 5, wherein the precise quantity of the tert-butyl alcohol (TBA) is completely consumed in the oligomerization reaction zone.

7. The process as claimed in claim 1, wherein the unconverted olefinic C4 feedstock is transferred to the oligomer product recovery column downstream of the pressure reduction zone.

8. The process as claimed in claim 1, wherein in the alcohol recovery column, unreacted water along with lighter components is collected at a top of the alcohol recovery column, the unreacted water is removed by a decantation process.

9. The process as claimed in claim 8, wherein the oligomerization reaction zone without any unreacted water protects the ion exchange resin catalyst from deactivation.

10. The process as claimed in claim 1, wherein the pressure reduction zone reduces the pressure of the oligomerization product stream to 5-7 bar.

11. The process as claimed in claim 1, wherein the oligomer product recovery column separates a pressure reduction zone stream into an unreacted olefinic C4 component and an oligomer product.

12. The process as claimed in claim 11, wherein the unreacted olefinic C4 component is transferred to the oligomerization reaction zone, wherein, the unreacted olefinic C4 component acts as a coolant to remove the exotherm in the oligomerization reaction zone and to increase the overall yield of the oligomer product.

13. The process as claimed in claim 1, wherein the ratio of the first stream passing through a hydration reaction zone and the second stream passing through an oligomerization reaction zone ranges from 0.01:1 to 0.3:1.

14. An apparatus for simultaneous production of alcohols and oligomers from an olefinic C4 feedstock, wherein the apparatus comprises:
  a de-metallization reaction zone for removing at least one impurity component from the olefinic C4 feedstock, wherein the olefinic C4 feedstock as obtained from the de-metallization reaction zone is divided into a first stream, and a second stream which passes through a mixer to provide a mixer stream;
  a hydration reaction zone to carry out a hydration reaction in the presence of an acidic catalyst and water, wherein the hydration reaction converts the olefinic C4 feedstock of the first stream into heavier products comprising a mixture of a plurality of alcohol compounds, and a plurality of oligomer products;
  an alcohol recovery column to separate the heavier products from an unconverted olefinic C4 feedstock; and
  an oligomerization reaction zone to carry out an oligomerization reaction of a mixer stream in presence of an ion exchange resin catalyst, wherein the oligomerization reaction zone output an oligomerization product stream, wherein a mixer provides the mixer stream comprising the second stream and a precise quantity of recovered alcohol from the alcohol recovery column.

15. The apparatus as claimed in claim 14, wherein the apparatus comprises an oligomer product recovery column and a pressure reduction zone, wherein, the oligomerization product stream passes through the pressure reduction zone before going into the oligomer product recovery column.

16. The apparatus as claimed in claim 15, wherein the pressure reduction zone reduces the pressure of the oligomerization product stream to 5-7 bar.

17. The apparatus as claimed in claim 14, wherein the plurality of alcohol compounds comprises a tert-butyl alcohol (TBA), and other lighter alcohols, wherein, the tert-butyl alcohol (TB A) form azeotropes with hydrocarbons of the olefinic C4 feedstock and having freezing point below 25° C.

18. The apparatus as claimed in claim 14, wherein a precise quantity of the tert-butyl alcohol (TB A) is transferred to the oligomerization reaction zone after mixing with an olefinic C4 feedstock of the second stream in the mixer, and an extra quantity of the tert-butyl alcohol (TBA) is transferred to a storage unit.

19. The apparatus as claimed in claim 14, wherein the unconverted olefinic C4 feedstock is transferred to the oligomer product recovery column downstream of a pressure reduction zone.

20. The apparatus as claimed in claim 14, wherein in the alcohol recovery column an unreacted water along with lighter components is collected at top of the alcohol recovery column, the unreacted water is removed by a decantation process.

* * * * *